US006197346B1

(12) United States Patent
Mathiowitz et al.

(10) Patent No.: US 6,197,346 B1
(45) Date of Patent: Mar. 6, 2001

(54) BIOADHESIVE MICROSPHERES AND THEIR USE AS DRUG DELIVERY AND IMAGING SYSTEMS

(75) Inventors: Edith Mathiowitz, Brookline, MA (US); Donald Chickering, Providence, RI (US); Jules Serge Jacob, Fall River, MA (US)

(73) Assignee: Brown Universtiy Research Foundation, Providence, RI (US)

( * ) Notice: Subject to any disclaimer, the term of this patent is extended or adjusted under 35 U.S.C. 154(b) by 0 days.

(21) Appl. No.: 07/873,480

(22) Filed: Apr. 24, 1992

(51) Int. Cl.$^7$ .............................. A61K 9/16; A61K 51/12
(52) U.S. Cl. ..................... 424/493; 424/497; 424/499; 424/501; 424/1.29
(58) Field of Search .......................... 424/490, 491–497, 424/499–501, 426, 428, 1.29

(56) References Cited

U.S. PATENT DOCUMENTS

| | | | |
|---|---|---|---|
| 4,959,219 | * 9/1990 | Chow et al. | 424/495 |
| 4,976,968 | 12/1990 | Steiner | 424/491 |
| 5,069,936 | * 12/1991 | Yen | 424/491 |
| 5,200,181 | * 4/1993 | Soltys et al. | 424/489 |

FOREIGN PATENT DOCUMENTS

| | | |
|---|---|---|
| 0 333 523 | 9/1989 | (EP) . |
| PCT/US90/06430 | 5/1990 | (WO) . |
| PCT/US90/06433 | 5/1990 | (WO) . |

OTHER PUBLICATIONS

D. Duchene, et al., "Pharmaceutical and Medical Aspects of Bioadhesive Systems for Drug Administration" *Drug Dev. Ind. Pharm.*, 14(2&3), 293–318 (1988).

Smart, et al., "An in–vitro investigation of mucosa–adhesive materials for use in controlled drug delivery", *J. Pharm. Pharmacol.* 36:295–299 (1984).

K. Park, et al., "Alternative Approaches to Oral Drug Controlled Drug Delivery: Bioadhesives and In–Situ Systems" 163–183 J. M.Anderson and S. W. Kim, ed., Recent Advances in Drug Delivery (Plenum Press NY 1984).

A. Mikos, et al. "Interaction of Polymer Microspheres with Mucin Gels as a Means of Characterizing Polymer Retention on Mucus" *J. Colloid Interface Sci.*, 143, 2:366–373 (May 1991).

R. Gurny, et al. "Bioadhesive intraoral release systems: design, testing and analysis", *Biomaterials* 5, 336–340 (1984).

Lehr, et al. "Intestinal Transit of Bioadhesive Microspheres in an In Situ Loop in the Rate–A Comparative Study with Copolymers and Blends Based on Poly(acrylic acid)" *J. Controlled Rel. Soc.* 13:51–62 (1990).

* cited by examiner

Primary Examiner—Edward J. Webman
(74) Attorney, Agent, or Firm—Arnall Golden & Gregory, LLP

(57) ABSTRACT

Bioadhesive polymers in the form of, or as a coating on, microcapsules containing drugs or bioactive substances which may serve for therapeutic, diagnostic, or diagnostic purposes in diseases of the gastrointestinal tract, are described. The polymeric microspheres all have a bioadhesive force of at least 11 mN/cm$^2$ (110 N/CM$^2$). Techniques for the fabrication of bioadhesive microspheres, as well as a method for measuring bioadhesive forces between microspheres and selected segments of the gastrointestinal tract in vitro are also described. This quantitative method provides a means to establish a correlation between the chemical nature, the surface morphology and the dimensions of drug-loaded microspheres on one hand and bioadhesive forces on the other, allowing the screening of the most promising materials from a relatively large group of natural and synthetic polymers which, from theoretical consideration, should be used for making bioadhesive microspheres.

11 Claims, 9 Drawing Sheets

BIOADHESIVE MICROSPHERES AND THEIR USE AS DRUG DELIVERY AND IMAGING SYSTEMS

BACKGROUND OF THE INVENTION

This invention is generally in the area of drug delivery systems, especially in the area of oral, rectal, vaginal and nasal drug delivery.

Drug delivery takes a variety of forms, depending on the agent to be delivered and the administration route. A preferred mode of administration is non-invasive; i.e., administration via nasal or oral passages. Some compounds are not suited for such administration, however, since they are degraded by conditions in the gastrointestinal tract or do not penetrate well into the blood stream.

Controlled release systems for drug delivery are often designed to administer drugs in specific areas of the body. In the gastrointestinal tract it is critical that the drug not be entrained beyond the desired site of action and eliminated before it has had a chance to exert a topical effect or to pass into the bloodstream. If a drug delivery system can be made to adhere to the lining of the appropriate viscus, its contents will be delivered to the targeted tissue as a function of proximity and duration of the contact.

There are two major aspects to the development of an adhesive bond between a polymer and the gastrointestinal tissue: (i) the surface characteristics of the bioadhesive material, and (ii) the nature of the biological material with which the polymer comes in contact. The intestinal mucosa is formed of a continuous sheet of epithelial cells of absorptive and mucin-recruiting cells. Overlying the mucosa is a discontinuous protective coating, the mucus, which is made of more than 95% water, as well as electrolytes, proteins, lipids and glycoproteins—the latter being responsible for the gel-like characteristics of the mucus. These glycoproteins consist of a protein core with covalently attached carbohydrate chains terminating in either sialic acid or L-fucose groups. The carbohydrate structure of the intestinal mucous glycoproteins is similar to that of the glycoproteins which are part of the epithelial cell membrane. The mucous glycoproteins act as "dummy receptors" for carbohydrate binding ligands which have evolved in nature to allow microorganisms and parasites to establish themselves on the gut wall. One function of the mucus is to intercept these ligands and associated infective agents and thereby protect the mucosa.

An orally ingested product can adhere to either the epithelial surface or the mucus. For the delivery of bioactive substances, it would be advantageous to have a polymeric device adhere to the epithelium rather than the mucous layer. For some types of imaging purposes, adhesion to both the epithelium and mucus is desirable whereas in pathological states, such as in the case of gastric ulcers or ulcerative colitis, adhesion to cells below the mucosa may be unavoidable.

Bioadhesion in the gastrointestinal tract proceeds in two stages: (1) viscoelastic deformation at the point of contact of the synthetic material into the mucus substrate, and (2) formation of bonds between the adhesive synthetic material and the mucus or the epithelial cells.

Several microsphere formulations have been proposed as a means for oral drug delivery. These formulations generally serve to protect the encapsulated compound and to deliver the compound into the blood stream. Enteric coated formulations have been widely used for many years to protect drugs administered orally, as well as to delay release. Other formulations designed to deliver compounds into the blood stream, as well as to protect the encapsulated drug, are formed of a hydrophobic protein, such as zein, as described in PCT/US90/06430 and PCT/US90/06433; "proteinoids", as described in U.S. Pat. No. 4,976,968 to Steiner; or synthetic polymers, as described in European Patent application 0 333 523 by The UAB Research Foundation and Southern Research Institute. EPA 0 333 523 describes microparticles of less than ten microns in diameter that contain antigens, for use in oral administration of vaccines. The microparticles are formed of polymers such as poly(lactide-co-glycolide), poly(glycolide), polyorthoesters, poly(esteramides), polyhydroxybutyric acid and polyanhydrides, and are absorbed through the Peyer's Patches in the intestine.

It would be advantageous if there was a method or means for increasing the absorption of these particles through the mucosal lining, or for delaying still further transit of the particles through the nasal or gastrointestinal passages.

Duchene, et al., *Drug Dev. Ind. Pharm.* 14(2&3), 283–318 (1988), reviews the pharmaceutical and medical aspects of bioadhesive systems for drug delivery. "Bioadhesion" is defined as the ability of a material to adhere to a biological tissue for an extended period of time. Bioadhesion is clearly one solution to the problem of inadequate residence time resulting from the stomach emptying and intestinal peristalsis, and from displacement by ciliary movement. For bioadhesion to occur, an intimate contact must exist between the bioadhesive and the receptor tissue, the bioadhesive must penetrate into the crevice of the tissue surface and/or mucus, and chemical bonds must form. Bioadhesive power of the polymers is affected by both the nature of the polymer and by the nature of the surrounding media.

Duchene, et al., tested polymers for bioadhesion by measuring the surface tension between a plate containing a mucous sample and a polymer coated glass plate. They review other systems using intestinal membrane rather than a mucosal solution, and in vivo studies using rats and radiolabeled polymeric material in a gelatin capsule. A number of polymers were characterized as to their bioadhesive properties but primarily in terms of "excellent" or "poor". Polycarbophils and acrylic acid polymers were noted as having the best adhesive properties, although the highest adhesive forces were still less than 10 mN/cm$^2$.

Others have explored the use of bioadhesive polymers. Smart, et al., *J. Pharm. Pharmacol.* 36:295–299 (1984), reported on a method to test adhesion to mucosa using a polymer coated glass plate contacting a dish of mucosa. A variety of polymeric materials were tested, including sodium alginate, sodium carboxymethylcellulose, gelatin, pectin, and polyvinylpyrrolidone. Gurney, et al., *Biomaterials* 5, 336–340 (1984), concluded that adhesion may be effected by physical or mechanical bonds; secondary chemical bonds; and/or primary, ionic or covalent bonds. Park, et al., *Alternative Approaches to Oral Controlled Drug Delivery: Bioadhesives and In-Situ Systems* 163–183 J. M. Anderson and S. W. Kim, ed., *Recent Advances in Drug Delivery* (Plenum Press N.Y. 1984), report on the use of fluorescent probes in cells to determine adhesiveness of polymers to mucin/epithelial surfaces. Their results indicated that anionic polymers with high charge density appear to be preferred as adhesive polymers.

None of these studies involved the study of tensile measurement between microspheres and intestinal tissue. Microspheres will be affected by other factors, such as the mucosal flow, peristaltic motion, high surface area to volume ratio.

Mikos, et al., in *J. Colloid Interface Sci.* 143, 2:366–373 (May 1991) and Lehr, et al., *J. Controlled Rel. Soc.* 13:51–62 (1990), both disclose the bioadhesive properties of polymers used for drug delivery: polyanhydrides and polyacrylic acid, respectively. Mikos, et al., report that the bioadhesive forces are a function of surface area, and are significant only for particles in excess of 900 microns in diameter (having an adhesive force of 120 $\mu$N, equivalent to 10.9 mN/cm$^2$), when measured in vitro. However, they also note that this may not be an adequate adhesive force in vivo, since the larger particle size is also subjected to greater flow conditions along the mucosa which may serve to displace these larger particles. In addition, Mikos, et al., found very small forces for particles smaller than 750 $\mu$. Lehr, et al., screened two commercially available microparticles of a diameter in excess of 500 microns formed of copolymers of acrylic acid, using an in vitro system, and determined that one copolymer "polycarbophil" increased adhesion over a control but that the other polymer did not. Polymeric coatings were also applied to polyhydroxyethylmethacrylic acid and tested in an in vivo model. As shown in Table 1, the maximum adhesive force was approximately 9 mN/cm$^2$ for polycarbophil.

Most prior art techniques for measuring in vitro bioadhesion are based on tensile experiments. These techniques were mainly designed for large tablets or polymer coated onto glass plates. Only a few in vitro techniques for direct measurement of adhesion forces between individual microcapsules and intestinal tissue are known. Some publications used a flow channel method. However, the only reported results are static measurements where the mucoadhesive force exerted on each particle was determined by placing small particles over intestinal mucosa and measuring the immersed surface area and the directional contact angles using video microscopy, by Mikos, et al.

It is therefore an object of the present invention to provide bioadhesive polymeric microspheres that are useful for drug delivery via the mucosal membranes.

It is a further object of the present invention to provide polymeric microspheres which can be used for imaging studies.

It is another object of the present invention to provide a method for determining bioadhesiveness of polymeric microspheres.

SUMMARY OF THE INVENTION

Bioadhesive polymers in the form of, or as a coating on, microcapsules containing drugs or bioactive substances which may serve for therapeutic, diagnostic, or diagnostic purposes in diseases of the gastrointestinal tract, are described. The polymeric microspheres all have a bioadhesive force of at least 11 mN/cm$^2$ (110 N/CM$^2$). Techniques for the fabrication of bioadhesive microspheres, as well as a method for measuring bioadhesive forces between microspheres and selected segments of the gastrointestinal tract in vitro are also described. This quantitative method provides a means to establish a correlation between the chemical nature, the surface morphology and the dimensions of drug-loaded microspheres on one hand and bioadhesive forces on the other, allowing the screening of the most promising materials from a relatively large group of natural and synthetic polymers which, from theoretical consideration, should be used for making bioadhesive microspheres.

These methods and materials are particularly useful for the oral administration of a wide range of drugs, particularly sulfonamides (e.g., sulfasalazine) and glycocorticoids (e.g., betamethasone), all of which are being used for treatment of bowel diseases. Bioadhesive microspheres containing barium sulphate for use in imaging have the following advantages over conventional administration of barium: (1) produce more uniform coverage as well as better adhesion of the barium to the mucosa in the stomach and the intestine, (2) eliminate the problem of barium sulphate precipitation by protecting it from the local pH. Encapsulation of radio-opaque materials and drugs in the same type of polymer but in different microcapsules and simultaneous administration of both type of microcapsules could provide a useful tool for studying the exact location of the delivery system in the GI tract.

BRIEF DESCRIPTION OF THE DRAWINGS

FIG. 5b is a graph for force of detachment per projected surface area versus microsphere diameter for P(FA:SA) microspheres. In this figure, the values from FIG. 3c have been normalized by the projected surface areas as described in FIG. 3a.

DETAILED DESCRIPTION OF THE INVENTION

Figure 1:
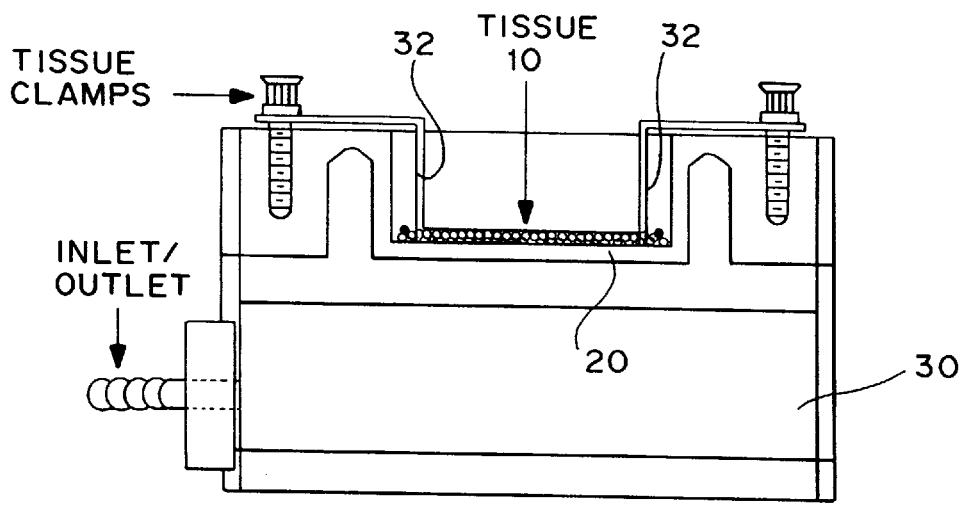
FIG. 1 is a perspective view of a tissue chamber used to measure bioadhesive forces of polymeric microspheres.

In general terms, adhesion of polymers to tissues may be achieved by (i) physical or mechanical bonds, (ii) primary or covalent chemical bonds, and/or (iii) secondary chemical bonds (i.e., ionic). Physical or mechanical bonds can result from deposition and inclusion of the adhesive material in the crevices of the mucus or the folds of the mucosa. Secondary chemical bonds, contributing to bioadhesive properties, consist of dispersive interactions (i.e., Van der Waals interactions) and stronger specific interactions, which include hydrogen bonds. The hydrophilic functional groups responsible for forming hydrogen bonds are the hydroxyl (—OH) and the carboxylic groups (—COOH).

Adhesive microspheres have been selected on the basis of the physical and chemical bonds formed as a function of chemical composition and physical characteristics, such as surface area, as described in detail below. These microspheres are characterized by adhesive forces to mucosa of greater than 11 mN/cm$^2$.

Classes of Polymers Useful in Forming Bioadhesive Microspheres.

Suitable polymers that can be used to form bioadhesive microspheres include soluble and insoluble, nonbiodegradable and biodegradable polymers. These can be hydrogels or thermoplastics, homopolymers, copolymers or blends, natural or synthetic. A key feature, however, is that the polymer must have a bioadhesive force of between 110 N/m$^2$ (11 mN/cm$^2$) and 5000 N/m$^2$ to a mucosal membrane of a patient.

Two classes of polymers appear to have potentially useful bioadhesive properties: hydrophilic polymers and hydrogels. In the large class of hydrophilic polymers, those containing carboxylic groups (e.g., poly[acrylic acid]) exhibit the best bioadhesive properties. One could infer that polymers with the highest concentrations of carboxylic groups should be the materials of choice for bioadhesion on soft tissues. Other promising polymers were: sodium alginate, carboxymethylcellulose, hydroxymethylcellulose and methylcellulose. Some of these materials are water-soluble, while others are hydrogels. Hydrogels have often been used for bioadhesive drug delivery; however, one big drawback of using hydrogels is the lack of long-term stability during storage which is a problem for therapeutic applications.

Rapidly bioerodible polymers such as poly[lactide-co-glycolide], polyanhydrides, polyorthoesters—which would expose carboxylic groups on the external surface as their smooth surface erodes—are excellent candidates for bioadhesive drug delivery systems in the gastrointestinal tract. Biodegradable polymers are more stable than hydrogels. In addition, polymers containing labile bonds, such as polyanhydrides and polyesters, are well known for their hydrolytic reactivity. Their hydrolytic degradation rates can generally be altered by simple changes in the polymer backbone.

Representative natural polymers are proteins, such as zein, serum albumin, or collagen, and polysaccharides, such as cellulose, dextrans, and alginic acid. Representative synthetic polymers include polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes, polyurethanes, alkyl cellulose, hydroxyalkyl celluloses, cellulose ethers, cellulose esters, nitrocelluloses, polymers of acrylic and methacrylic esters, poly[lactide-co-glycolide], polyanhydrides, polyorthoester blends and copolymers thereof. Specific examples of these polymers include cellulose acetate, cellulose propionate, cellulose acetate butyrate, cellulose acetate phthalate, carboxymethyl cellulose, cellulose triacetate, cellulose sulphate, poly(methyl methacrylate), poly(ethyl methacylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly (ethylene glycol), poly(ethylene oxide), poly(ethylene terephthalate), poly(vinyl alcohols), poly(vinyl acetate), poly(vinyl chloride), polystyrene and polyvinylpyrrolidone, polyurethane, polylactides, poly(butyric acid), poly(valeric acid), poly[lactide-co-glycolide], polyanhydrides, polyorthoesters, poly(fumaric acid), and poly(maleic acid).

These polymers can be obtained from sources such as Sigma Chemical Co., St. Louis, Mo., Polysciences, Warrenton, Pa., Aldrich, Milwaukee, Wis., Fluka, Ronkonkoma, N.Y., and BioRad, Richmond, Calif.

In the studies detailed below, a variety of polymer microspheres were compared for adhesive force to mucosa. Negatively charged hydrogels, such as alginate and carboxymethylcellulose, that expose carboxylic groups on the surface, were selected, as well as some positively-charged hydrogels, such as chitosan. The rationale behind this choice is the fact that most cell membranes are actually negatively charged and there is still no definite conclusion as to what the most important property is in obtaining good bioadhesion to the wall of the gastrointestinal tract. Thermoplastic polymers: (a) non-erodible, neutral polystyrene, and (b) semicrystalline bioerodible polymers that generate carboxylic groups as they degrade—polylactides and polyanhydrides, were also selected. Polyanhydrides are good candidates for bioadhesive delivery systems since, as hydrolysis proceeds, more and more carboxylic groups are exposed to the external surface. Polylactides erode by bulk erosion; furthermore, the erosion is slower. In designing these systems as bioadhesive polymers, polymers that have high concentrations of carboxylic acid were preferred. This was done by using low molecular weight polymers (Mw 2000), since low molecular weight polymer contain high concentration of carboxylic acids at the end groups.

Measurement of Bioadhesive Studies Using a Tensile Technique

The adhesive forces between polymer microspheres and segments of intestinal rat tissue can be measured using the Cahn DCA-322, as shown in FIG. 1. Although this piece of equipment is designed for measuring contact angles and surface tensions using the Wilhelmy plate technique, it is also an extremely accurate microbalance. The DCA-322 system includes a microbalance stand assembly, a Cahn DACS computer, and an Okidata Microline 320 dot matrix printer. The microbalance unit consists of stationary sample and tare loops and a moving stage powered by a stepper motor. The balance can be operated with samples weighing up to 3.0 g, and has a sensitivity rated at 0.001 dynes. The stage speed can be adjusted from 20 to 264 $\mu$m/sec using the factory installed motor, or from 2–24 $\mu$m/sec using the optional slow motor. Adhesive forces were measured by attaching a polymer sample to one of the sample loops and placing an adhesive substrate 10, intestinal tissue, below it on the moving stage 20.

For adhesive measurements, 1.5 cm sections are cut from the excised intestine. These were then sliced lengthwise and spread flat, exposing the lumen side. The samples were then placed in a temperature-regulated chamber 30, clamped 32 at their edges, and covered with approximately 0.9 cm high level of phosphate buffer saline, as shown in FIG. 1. Physiologic conditions were maintained in the chamber. The chamber was then placed in the microbalance enclosure and a microsphere, mounted on a wire and hung from the sample loop of the microbalance, was brought in contact with the tissue. The microspheres were left in contact with the tissue for seven minutes with an applied force of approximately 0.25 mN and then pulled vertically away from the tissue sample while recording the required force for detachment. The contact area was estimated to be the surface area of the spherical cap defined by the depth of penetration of the bead below the surface level of the tissue. The force values were normalized by the projected area of this cap (Area=$\pi R^2 - \pi (R-a)^2$, where R is the microsphere radius and a is the depth of penetration. For microspheres larger than 800 $\mu$m, a=400 m was used, for smaller microspheres a=R was used.

Figure 2:
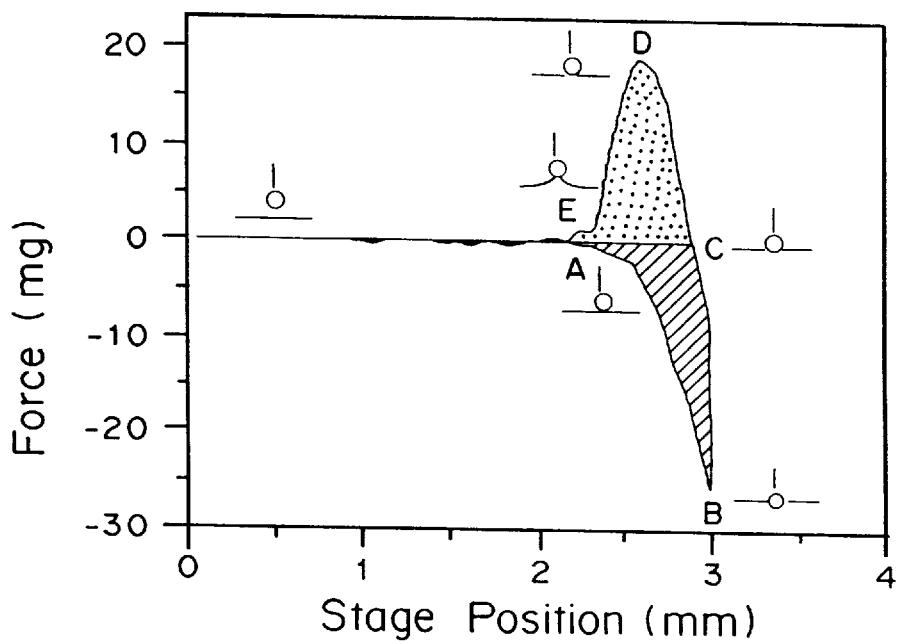
FIG. 2 is a graph of force (mg) versus stage position (mm) for a typical P(CPP:SA) microsphere.

Graphs of force versus distance as well as force versus time were studied. FIG. 2 shows a typical graph of force versus stage position for the P(CPP-SA) 20:80 microspheres. Point A in FIG. 2 indicates the applied force, which can be varied in each experiment, and which indirectly affects the degree of penetration into the tissue. Portion AB indicates the adhesion time, the time the sphere is left to interact with the tissue before movement of the stage is started to separate the surfaces. Segment BC indicates the elevation of the sphere to 0 mg applied force (point C). During the early part of the tensile experiment (CD), the force increases as a function of stage position, while the contact area between the sphere and the mucus is assumed to be constant and equal to the surface of the immersed sphere. The next portion of this curve (DE) indicates a period where partial detachment of the polymeric device from the mucus occurred with some changes in the contact area. The last point (E) is the detachment of the sphere from the mucus. In some cases, a detachment does not occur until the microsphere has been moved to a height of 4 mm above the initial level of contact.

From these graphs it is possible to determine the maximum force applied to the sample, the maximum adhesive force, the distance required for detachment of the samples and the work of adhesion (the surface under the force versus stage position curves CDE). More importantly, it allows quantification of the adhesive forces of a variety of individual microspheres and correlation of these forces with physical and chemical properties of the polymers.

Modification of Bioadhesive Polymers to Increase Bioadhesive Force.

The polymers are selected from commercially available polymers based on their adhesive properties using the method described above to determine those polymers forming microspheres (either as solid polymer or as a polymeric coating on a different material) having an adhesive force greater than 11 nN/mg$^2$. The microspheres are then formed having an appropriate surface area to provide the desired adhesive forces. The polymers (or polymeric surface) can also be modified as described below to increase the bioadhesive properties of the polymer.

For example, the polymers can be modified by increasing the number of carboxylic groups accessible during biodegradation, or on the polymer surface. The polymers can also be modified by binding amino groups to the polymer.

The attachment of polyethyleneimine or polylysine-coated acrylamide beads to intestine is probably due to the electrostatic attraction of the cationic groups coating the beads to the net negative charge of the mucus. The mucopolysaccharides and mucoproteins of the mucin layer, especially the sialic acid residues, are responsible for the negative charge coating. Any ligand with a high binding affinity for mucin could also be covalently linked to most microspheres with the appropriate chemistry, such as CDI, and be expected to influence the binding of microspheres to the gut. The ligand affinity need not be based only on electrostatic charge, but other useful physical parameters such as solubility in mucin or else specific affinity to carbohydrate groups.

The covalent attachment of any of the natural components of mucin in either pure or partially purified form to the microspheres would decrease the surface tension of the bead-gut interface and increase the solubility of the bead in the mucin layer. The list of useful ligands would include but not be limited to the following: sialic acid, neuraminic acid, n-acetyl-neuraminic acid, n-glycolylneuraminic acid, 4-acetyl-n-acetylneuraminic acid, diacetyl-n-acetylneuraminic acid, glucuronic acid, iduronic acid, galactose, glucose, mannose, fucose, or else any of the partially purified fractions prepared by chemical treatment of naturally occurring mucin, e.g., mucoproteins, mucopolysaccharides and mucopolysaccharide-protein complexes.

The covalent attachment of lectins to microspheres would also increase the affinity of the spheres to components of the mucin and mucosal cell layer. Useful lectin ligands include lectins isolated from: *Abrus precatroius, Agaricus bisporus, Anguilla anguilla, Arachis hypogaea, Pandeiraea simplicifolia, Bauhinia purpurea, Caragan arobrescens, Cicer arietinum, Codium fragile, Datura stramonium, Dolichos biflorus, Erythrina corallodendron, Erythrina cristagalli, Euonymus europaeus, Glycine max, Helix aspersa, Helix pomatia, Lathyrus odoratus, Lens culinaris, Limulus polyphemus, Lysopersicon esculentum, Maclura pomifera, Momordica charantia, Mycoplasma gallisepticum, Naja mocambique*, as well as the lectins Concanavalin A and Succinyl-Concanavalin A.

Formation of Microspheres.

As used herein, microspheres includes microparticles and microcapsules (having a core of a different material than the outer wall), having a diameter in the nanometer range up to 1 mm. The microsphere may consist entirely of bioadhesive polymer or have only an outer coating of bioadhesive polymer.

Microspheres have been fabricated from the different polymers. Polylactic blank microspheres were fabricated by using two methods: solvent evaporation, as described by E. Mathiowitz, et al., *J. Scanning Microscopy*, 4, 329 (1990); L. R. Beck, et al., *Fertil. Steril.*, 31, 545 (1979); and S. Benita, et al., *J. Pharm. Sci.*, 73, 1721 (1984); and hot-melt microencapsulation, as described by E. Mathiowitz, et al., *Reactive Polymers*, 6, 275 (1987). Polyanhydrides made of bis-carboxyphenoxypropane and sebacic acid with molar ratio of 20:80 (P(CPP-SA) 20:80) (Mw 20,000) were prepared by hot-melt microencapsulation. Poly(fumaric-co-sebacic) (20:80) (Mw 15,000) blank microspheres were prepared by hot-melt microencapsulation. Polystyrene microspheres were prepared by solvent evaporation.

Hydrogel microspheres were prepared by dripping the solution from a reservoir though a 250 microliter pipet tip into a stirred ionic bath. The specific conditions for alginate, chitosan, alginate/polyethylenimide (PEI) and carboxymethyl cellulose (CMC) are listed in Table 1.

a. Solvent Evaporation. In this method the polymer is dissolved in a volatile organic solvent, methylene chloride. The drug (either soluble or dispersed as fine particles) is added to the solution, and the mixture is suspended in an aqueous solution that contains a surface active agent such as poly(vinyl alcohol). The resulting emulsion is stirred until most of the organic solvent evaporates, leaving solid microspheres. Several different polymer concentrations will be used (0.05–0.20 g/ml). The solution will be loaded with a drug and suspended in 200 ml of vigorously stirred distilled water containing 1% (w/v) poly(vinyl alcohol) (Sigma). After 4 hours of stirring, the organic solvent will have evaporated from the polymer, and the resulting microspheres are washed with water and dried overnight in a lyophilizer. Microspheres with different sizes (1–1000 microns) and morphologies can be obtained by this method. This method is useful for relatively stable polymers like polyesters and polystyrene.

However, labile polymers, such as polyanhydrides, may degrade during the fabrication process due to the presence of water. For these polymers, the following two methods, which are performed in completely organic solvents, are more useful.

b. Hot Melt Microencapsulation. In this method, the polymer is first melted and then mixed with the solid particles of the dye or drug that have been sieved to less than 50 microns. The mixture is suspended in a non-miscible solvent (like silicon oil), and, while stirring continuously, heated to 5° C. above the melting point of the polymer. Once the emulsion is stabilized, it is cooled until the polymer particles solidify. The resulting microspheres are washed by decantation with petroleum ether to give a free-flowing powder. Microspheres with sizes between one to 1000 microns can be obtained with this method. The external surfaces of spheres prepared with this technique are usually smooth and dense. This procedure is used to prepare microspheres made of polyesters and polyanhydrides. However, this method is limited to polymers with molecular weights between 1000–50000.

c. Solvent Removal. This technique was primarily designed for polyanhydrides. In this method, the drug is dispersed or dissolved in a solution of the selected polymer in a volatile organic solvent like methylene chloride. This mixture is suspended by stirring in an organic oil (such as silicon oil) to form an emulsion. Unlike solvent evaporation, this method can be used to make microspheres from polymers with high melting points and different molecular weights. Microspheres that range between 1–300 microns can be obtained by this procedure. The external morphology of spheres produced with this technique is highly dependent on the type of polymer used.

d. Hydrogel Microspheres. Microspheres made of gel-type polymers, such as alginate, are produced by dissolving the polymer in an aqueous solution, suspending the barium sulphate or any other active material in the mixture and extruding through a microdroplet forming device, producing microdroplets which fall into a hardening bath, that is slowly stirred. The advantage of these systems is the ability to further modify the surface of the microspheres by coating them with polycationic polymers, like polylysine after fabrication. Microsphere particles are controlled by using various size extruders. Table 1 summarizes the various hydrogels and the concentrations that were used to manufacture them.

TABLE 1

Type and Concentration for Hydrogels Fabrication

| Hydrogel | Hydrogel Conc. | Bath Type/Conc. | Stirring |
| --- | --- | --- | --- |
| Chitosan | 1.0% | Tripolyphosphate, 3% | 170 rpm |
| Alginate | 2.0% | Calcium Chloride, 1.3% | 160 rpm |
| Alginate/PEI | 2.0/6.0% | Calcium Chloride, 1.3% | 160 rpm |
| CMC | 2.0% | Lead Nitrate, 10% | 100 rpm |

Chitosan microspheres can be prepared by dissolving the polymer in acidic solution and crosslinking it with tripolyphosphate. Carboxymethyl cellulose (CMC) microspheres were prepared by dissolving the polymer in acid solution and precipitating the microsphere with lead ions. Alginate/polyethylene imide (PEI) were prepared in order to reduce the amount of carboxylic groups on the alginate microcapsule.

Materials that can be Incorporated into the Microspheres.

There is no specific limitation on the material that can be encapsulated within the bioadhesive polymer. Any kind of bioactive agent, including organic compounds, inorganic compounds, proteins, polysaccharides, or other materials can be incorporated using standard techniques.

Examples of useful proteins include hormones such as insulin, growth hormones including somatometins, transforming growth factors, and other growth factors, antigens for oral vaccines, enzymes such as lactase or lipases, and digestive aids such as pancreatin.

Examples of useful drugs include ulcer treatments such as Carafate from Marion Pharmaceuticals, antihypertensives or saluretics such as Metolazone from Searle Pharmaceuticals, carbonic anhydrase inhibitors such as Acetazolamide from Lederle Pharmaceuticals, insulin like drugs such as glyburide, a blood glucose lowering drug of the sulfonylurea class, hormones such as Android F from Brown Pharmaceuticals and Testred (methyltestosterone) from ICN Pharmaceuticals, antiparasitics such as mebeandazole (Vermox™, Jannsen Pharmaceutical. Other drugs for application to the vaginal lining or other mucosal membrane lined orifices such as the rectum include spermacides, yeast or trichomonas treatments and anti-hemorrhoidal treatments.

In a preferred method for imaging, a radiopaque material such as barium is coated with polymer. Radioactive materials or magnetic materials could be used in place or, or in addition to, the radiopaque materials.

Administration of Bioadhesive Microspheres to Patients.

The microspheres are administered in suspension or in ointment to the mucosal membranes, via the nose, mouth, rectum, or vagina. Pharmaceutically acceptable carriers for oral or topical administration are known and determined based on compatibility with the polymeric material. Other carriers include bulking agents such as Metamucil™.

These microspheres are especially useful for treatment of inflammatory bowel diseases such as ulcerative colitis and Crohn's disease. In ulcerative colitis, inflammation is restricted to the colon, whereas in Crohn's disease, inflammatory lesions may be found throughout the gastrointestinal tract, from the mouth to the rectum. Sulfasalazine is one of the drugs that is used for treatment of the above diseases. Sulfasalazine is cleaved by bacterial within the colon to sulfapyridine, an antibiotic, and to 5-amino salicylic acid, an anti-inflammatory agent. The 5-amino salicylic acid is the active drug and it is needed locally. Direct administration of the degradation product (5-amino salicylic acid) may be more beneficial. A bioadhesive drug delivery system could improve the therapy by retaining the drug for a prolonged time in the intestinal tract. For Crohn's disease, retention of 5-aminosalicylic acid in the upper intestine is of great importance, since bacteria cleave the sulfasalazin in colon, the only way to treat inflammations in the upper area is by local administration of 5-aminosalicylic acid.

Gastrointestinal Imaging Barium sulphate suspension is the universal contrast medium used for examination of the upper gastrointestinal tract, as described by D. Sutton, Editor, A Textbook of Radiology and Imaging, Volume 2, Churchill Livingstone, London (1980), even though it has undesirable properties, such as unpalatability and a tendency to precipitate out of solution.

Several properties are critical: (a) Particle size: the rate of sedimentation is proportional to particle size (i.e., the finer the particle, the more stable the suspension). (b) Non-ionic medium: charges on the barium sulphate particles influence the rate of aggregation of the particles. Aggregation is enhanced in the presence of the gastric contents. (c) Solution pH: suspension stability is best at pH 5.3. However, as the suspension passes through the stomach, it is inevitably acidified and tends to precipitate.

The encapsulation of barium sulfate in microspheres of appropriate size provides a good separation of individual contrast elements and may, if the polymer displays bioadhesive properties, help in coating, preferentially, the gastric mucosa in the presence of excessive gastric fluid. With bioadhesiveness targeted to more distal segments of the gastrointestinal tract, it may also provide a kind of wall imaging not easily obtained otherwise.

The double contrast technique, which utilizes both gas and barium sulphate to enhance the imaging process, especially requires a proper coating of the mucosal surface. To achieve a double contrast, air or carbon dioxide must be introduced. This is typically achieved via a nasogastric tube to provoke a controlled degree of gastric distension. Studies indicate that comparable results may be obtained by the release of individual gas bubbles in a large number of individual adhesive microspheres and that this imaging process may apply to intestinal segments beyond the stomach.

An in vivo method for evaluating bioadhesion uses encapsulation of a radiopaque material, such as barium sulphate, or a gas-evolving agent, such as sodium carbonate, within a bioadhesive polymer. After oral administration of this radiopaque material, its distribution in the gastric and intestinal areas is examined using image analysis.

The present invention will be further understood by reference to the following non-limiting examples.

EXAMPLE 1

Evaluation of Bioadhesive Properties of Polymeric Microspheres

Polymers were evaluated for their bioadhesive potential using microspheres with diameters ranging from 700–800 $\mu$m and 700–2400 $\mu$m for the thermoplastics and hydrogels, respectively. The tensile type experiment used in this study offers several advantages over previous techniques. The setup enables one to determine bioadhesive forces between a single microsphere and intestinal mucosa. Since the experiment was conducted in an aqueous environment, problems in distinguishing between surface tension forces at the air/liquid interface and forces at the microsphere/mucus interface were eliminated.

Figure 3A:
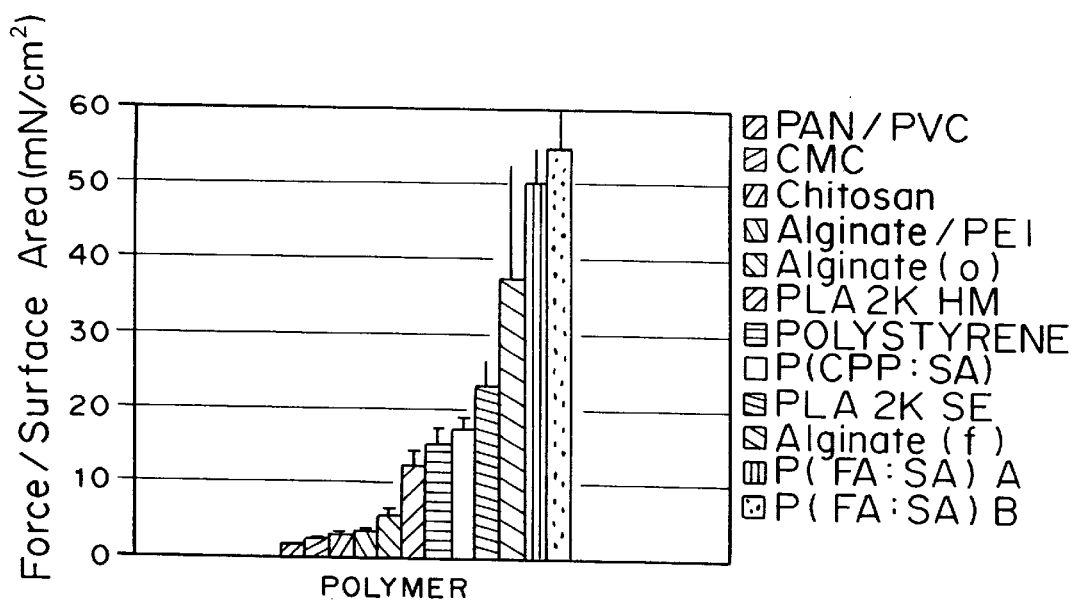
FIG. 3a is a graph of force of detachment per projected surface area (mN/cm$^2$) for various polymers. The polymers used in this study included the following: alginate (one sample prepared several hours prior to testing (alginate (f)) [diam.=700$\mu$] and another prepared several months prior to testing and left in a Ca$^+$solution (alginate (o)) [diam.=2400$\mu$]), alginate/polyethylene imide (alginate/PEI) [diam.=2100$\mu$], carboxymethylcellulose (CMC) [diam.=1800$\mu$], chitosan (high molecular weight) [diam.=2000$\mu$], polyacrylonitrile/polyvinyl chloride (PAN/PVC) [diam.=2900$\mu$], polylactic acid: MW=2,000 (one sample made by the hot melt technique (PLA 2K HM) [diam. =780$\mu$] and one sample made by the solvent evaporation technique (PLA 2K SE) [diam.=800$\mu$]), polystyrene [diam.=800$\mu$], poly[bis(p-carboxy phenoxy) propane-co-sebacic anhydride] made with sudan red dye (P(CPP:SA)) [diam.=780$\mu$], and poly[fumaricco-sebacic anhydride] (one sample made with acid orange dye (P(FA:SA)A) [diam.=780$\mu$] and one sample containing no dye (P(FA:SA) B [diam.=780$\mu$]). The forces were measured as the weight (mg) required to remove the microsphere from the intestinal tissue after a seven minute adhesion time using the Cahn electrobalance and converted to units of force (mN). These forces were then normalized by dividing by the surface area in contact with the tissue for each case. The surface areas were determined by the projection of the spherical cap of the microsphere that penetrated below the surface level of the tissue (Area=$\pi R^2 - \pi (R-a)^2$, where 'R' is the microsphere radius and 'a' is the depth of penetration). All force/surface area values are presented with the standard errors of measure (SEM).
Figure 3B:
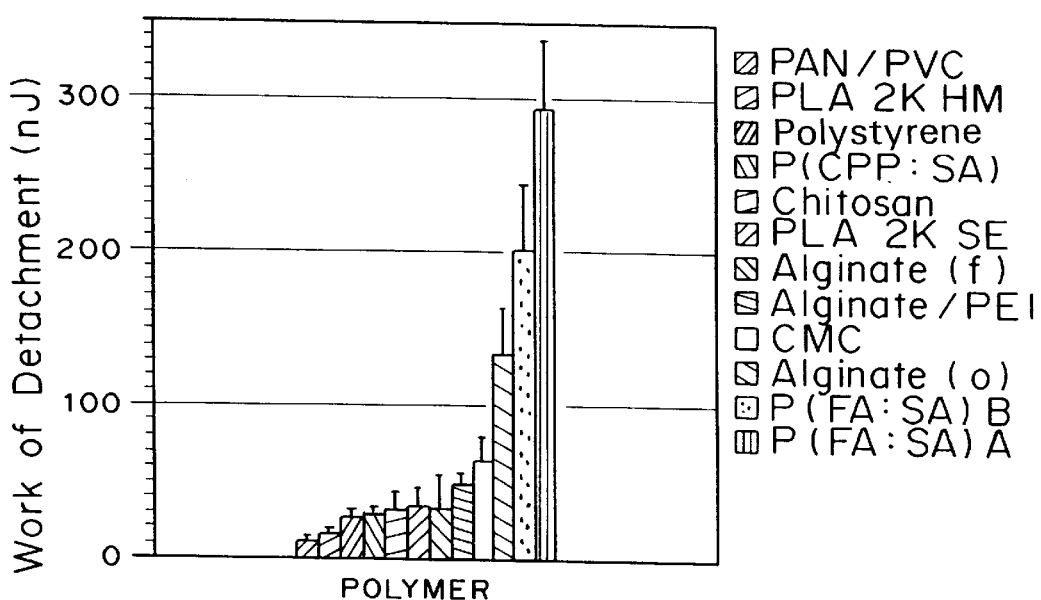
FIG. 3b is a graph of the work of detachment (nJ) for the polymeric microspheres described in FIG. 3a. Work values were determined from the areas beneath the curves of the force versus distance graphs produced with the Cahn electrobalance, and are presented with standard errors of measure.
Figure 3C:
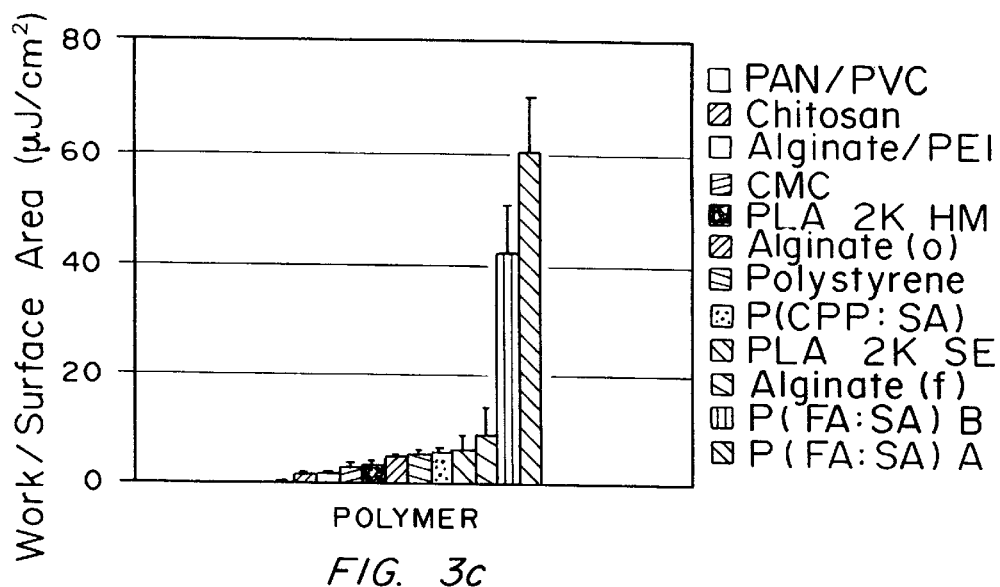
FIG. 3c is a graph of work of detachment per projected surface area (pJ/cm$^2$) for the polymeric microspheres described in FIG. 3a. All work/surface area values are presented with the standard errors of measure.
Figure 3D:
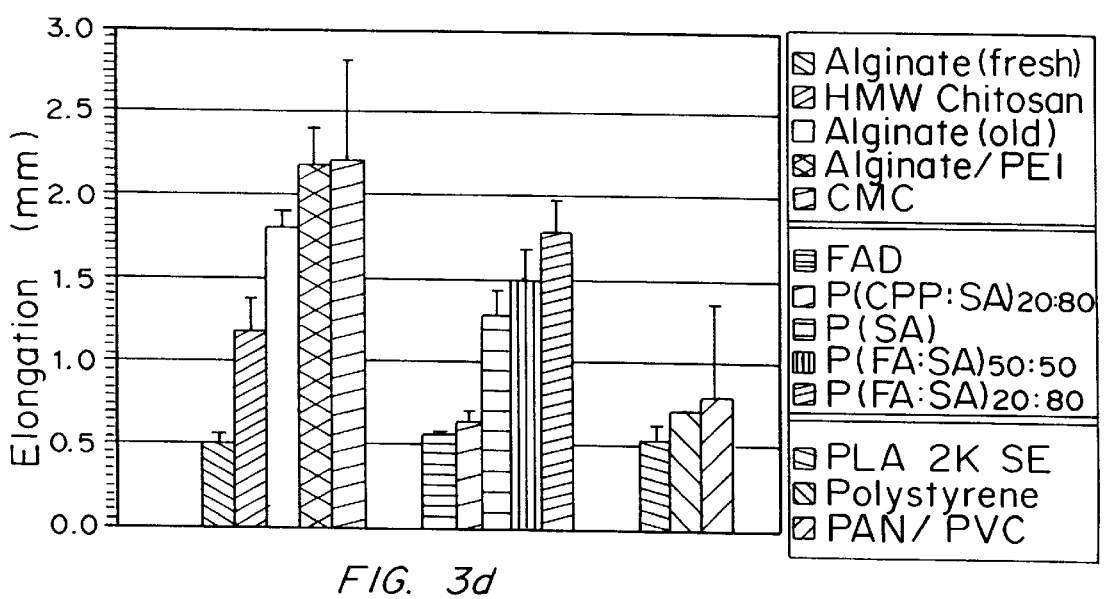
Figure 4A:
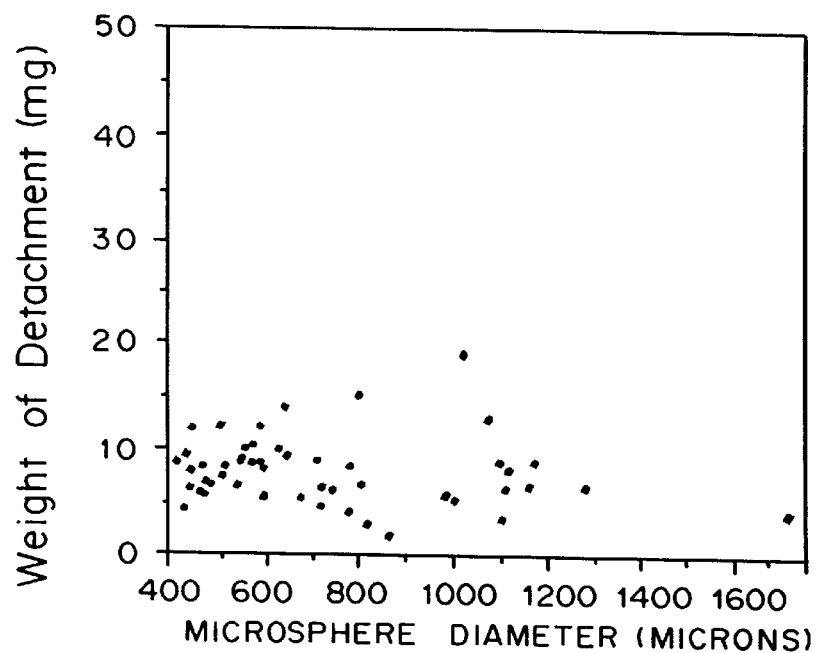
FIG. 4a is a graph of the weight of detachment versus Microsphere Diameter. The microspheres in this study were poly[bis(p-carboxy phenoxy) propane-co-sebacic anhydride] made with sudan red dye made by the hot melt technique. The microsphere diameters were measured with a micrometer prior to testing. The weight of detachment is the weight, measured by the Cahn electrobalance, which is required to remove the microsphere from the intestinal tissue after a seven minute adhesion time.
Figure 4B:
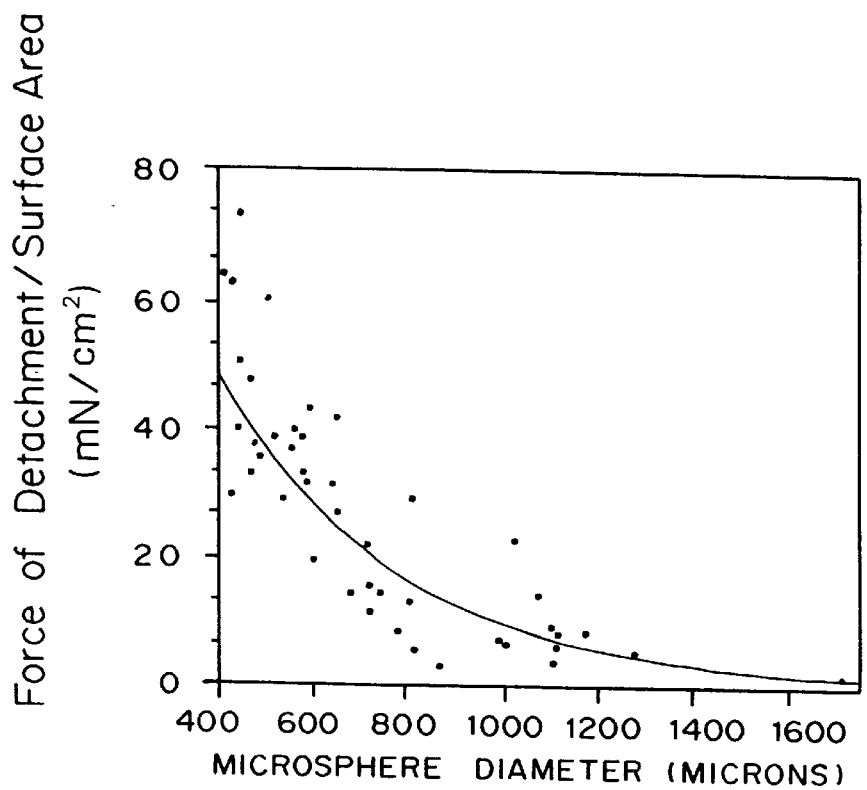
FIG. 4b is a graph of the force of detachment/surface area (mN/cm$^2$) versus microsphere diameter (microns) for p(CPP:SA) microspheres.
Figure 5A:
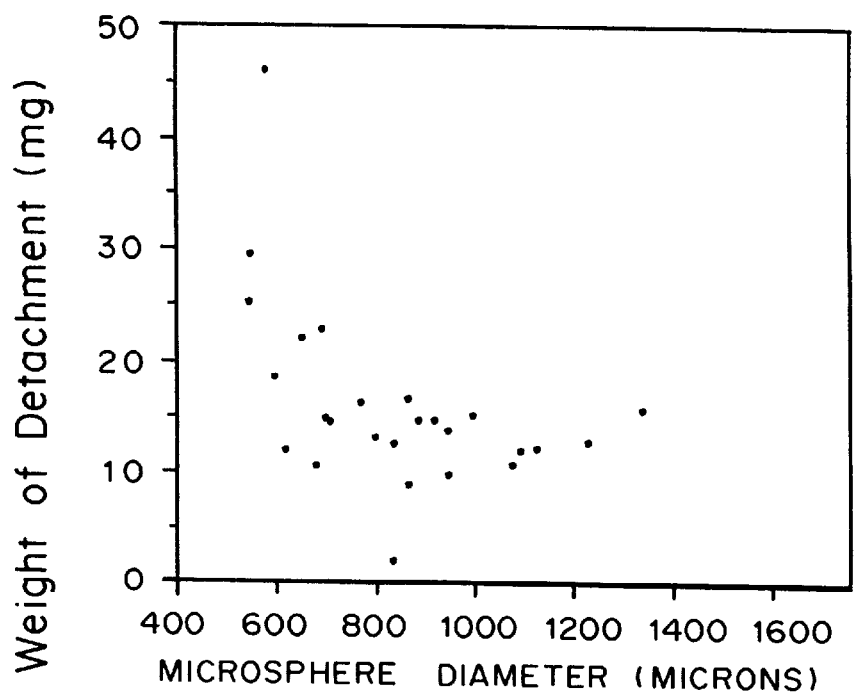
FIG. 5a is a graph of the weight of detachment (mg) versus microsphere diameter (microns) for poly[fumaric-co-sebacic anhydride] (p(FA:SA)) made by the hot melt technique. The microsphere diameters were measured with a micrometer prior to testing. The weight of detachment is the weight, measured by the Cahn electrobalance, which is required to remove the microsphere from the intestinal tissue after a seven minute adhesion time.
Figure 5B:
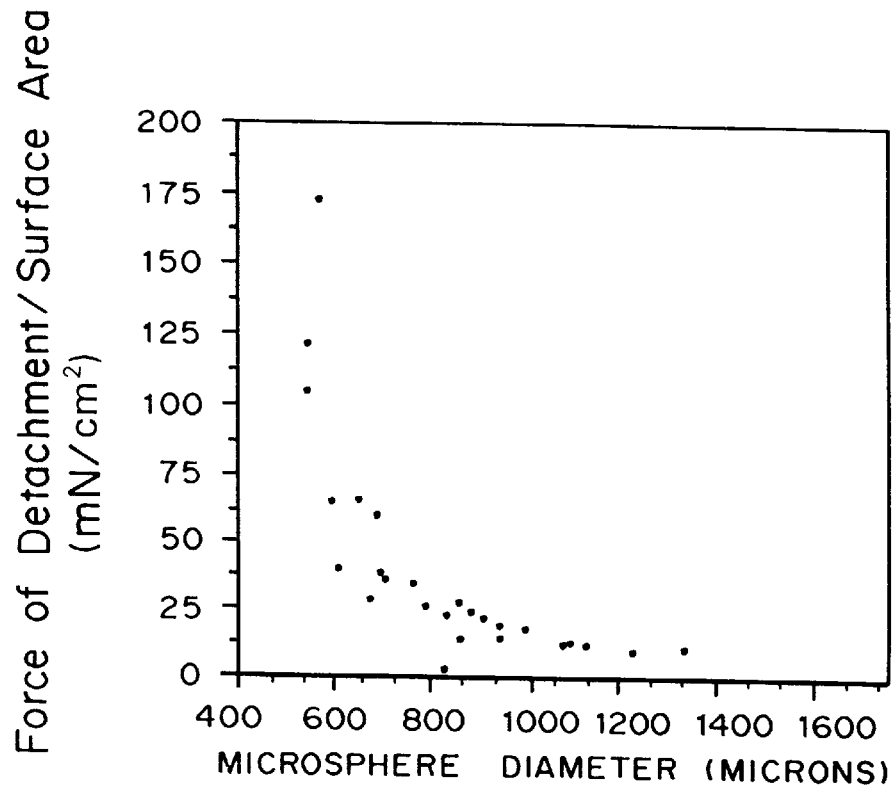

The results, shown in FIGS. 3a, 3b, and 3c, demonstrate that polymers with higher concentrations of carboxylic acid groups such as alginate and polyanhydrides, produce greater bioadhesive bonds. The extremely high forces obtain for poly(fumaric-co-sebacic) anhydride (20:80) (50 mN/cm$^2$) indicate that bioerodible polymers are very promising bioadhesive delivery systems.

The results also indicate that different fabrication methods which result in different morphologies exhibit different bioadhesive forces (e.g., PLA microspheres made by solvent evaporation adhere much stronger than PLA microspheres made by hot-melt microencapsulation). Comparison of the adhesive forces for polycarbophile, which was found to have good bioadhesive properties, show that polycarbophile displays bioadhesive forces of 1061 dyne/cm$^2$ (106.1 N/m$^2$ or 10.61 mN/cm$^2$) while most of the polymers described herein exhibit forces that range between 100 to 400 N/m$^2$.

EXAMPLE 2

Effect of Microsphere Diameter on Bioadhesive Forces.

The effect of microsphere diameter on bioadhesive forces was investigated using P(CPP:SA) 20:80 and P(FA:SA) 20:80 microspheres ranging in size from 400 $\mu$m to 1700 $\mu$m, using the method described above.

The results are shown in FIGS. 4a, 4b, 5a, and 5b. There was no decline in adhesive force with a decrease in microsphere diameter. To the contrary, the forces measured increase sharply as the diameters dropped below 750 $\mu$m to at least as low as 400 $\mu$m.

EXAMPLE 3

In Vivo Transit Time Studies Using X-ray Imaging of Non-releasing Microspheres.

A series of 10 rats were fed P(CPP-SA) 20:80 microspheres, as well as polystyrene microspheres, both loaded with barium sulphate. Each rat was fed 100 mg microspheres that were dispersed in 2 ml water. As controls, pure barium sulphate suspension in distilled water was fed to the rats. At given time intervals, the rats were X-rayed, and the distribution of the microspheres in the stomach and in the intestine was followed.

Figure 6A:
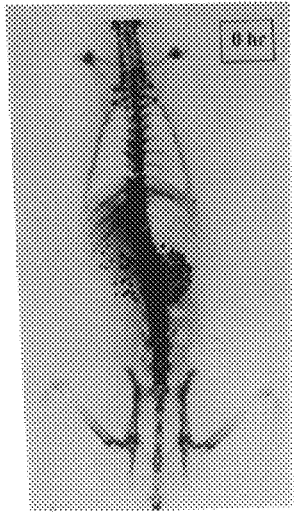
FIG. 6 is a X-ray print of rats fed with barium sulphate loaded P(CPP:SA) microspheres.
Figure 6B:
Figure 6C:
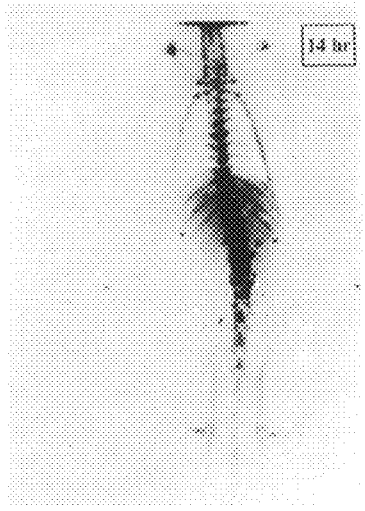
Figure 7A:
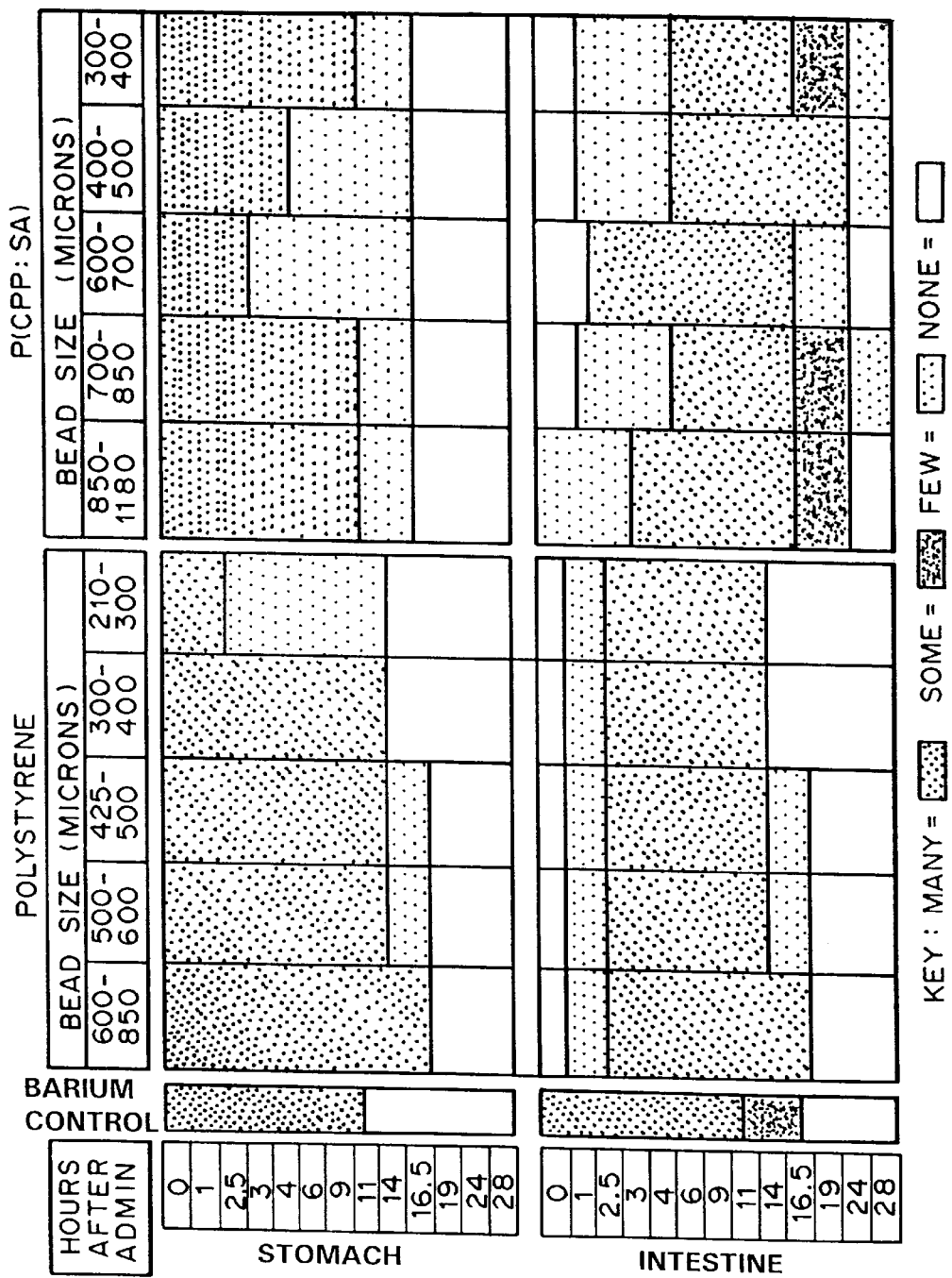
FIG. 7 is a graph of intestinal and stomach transit time (hours) for barium, polystyrene and P(CPP:SA) as a function of bead size (microns).
Figure 7C:
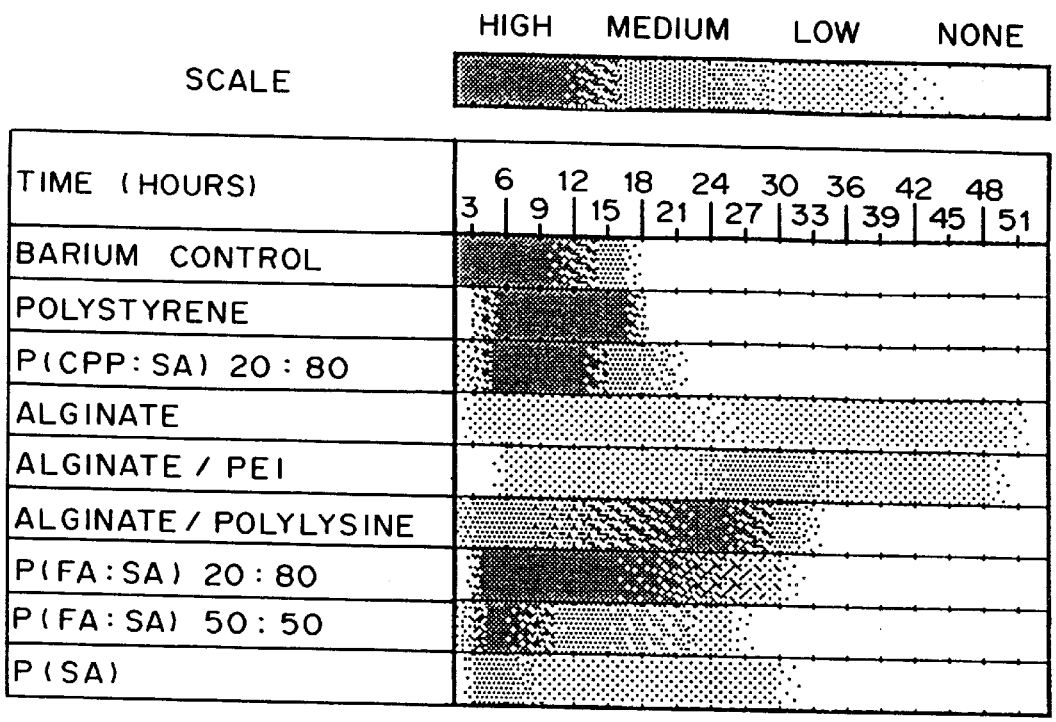
Figure 7B:
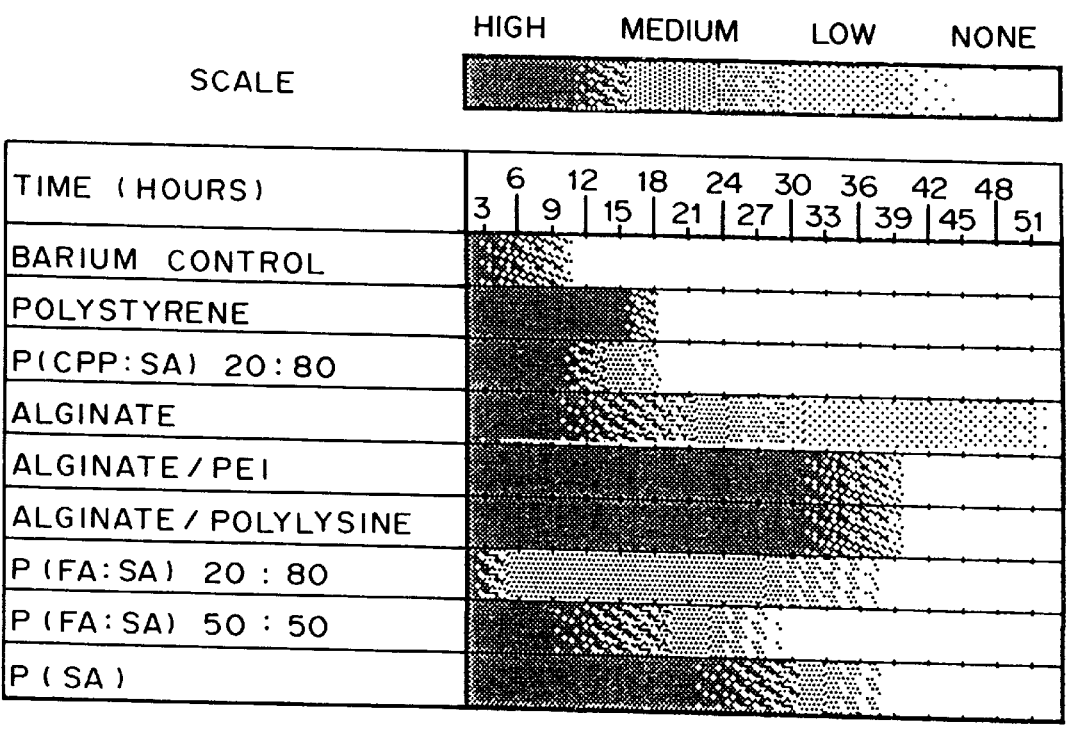

The results are shown in FIGS. 6 and 7. It was observed that the polyanhydride and polystyrene microspheres were retained in the stomach for 11 to 16.5 hours while the barium sulphate was cleared from the stomach after 9 hours. Most of the barium sulphate was cleared from the intestine after 14 to 16 hours. Polystyrene microspheres were cleared from the gastrointestinal tract after the same time interval. However, it was observed that polyanhydride microspheres could still be found in the intestine even after 28 hours. Since normal transit time through the intestinal tract ranges between 4 to 12 hours, the results with polyanhydrides suggest bioadhesion of the microspheres which delays their passage through the gastrointestinal system. It is apparent that the smaller microspheres tend to have a longer retention time in the intestine.

Comparing these results to the literature reveals that polycarbophiles with adhesive forces of 106 $N/m^2$ are retained 24 hr in the GI tract. Adhesive forces of about 200 $N/m^2$ yielded a retention time of 28 hr.

Figure 8A:
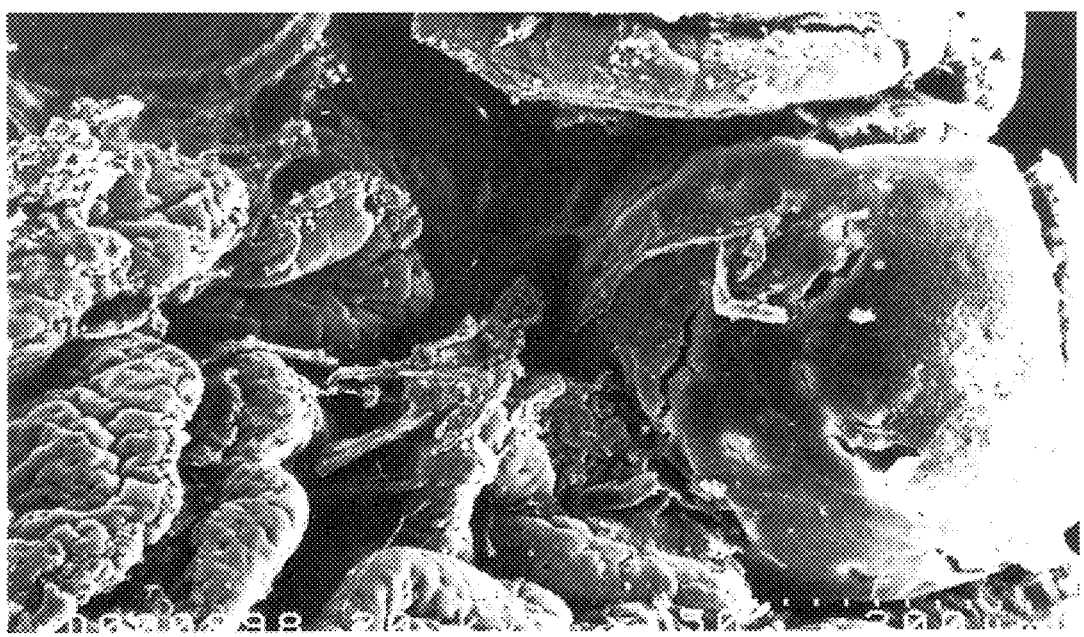
FIG. 8a is a SEM of microsphere adhering to the mucosa.
Figure 8B:
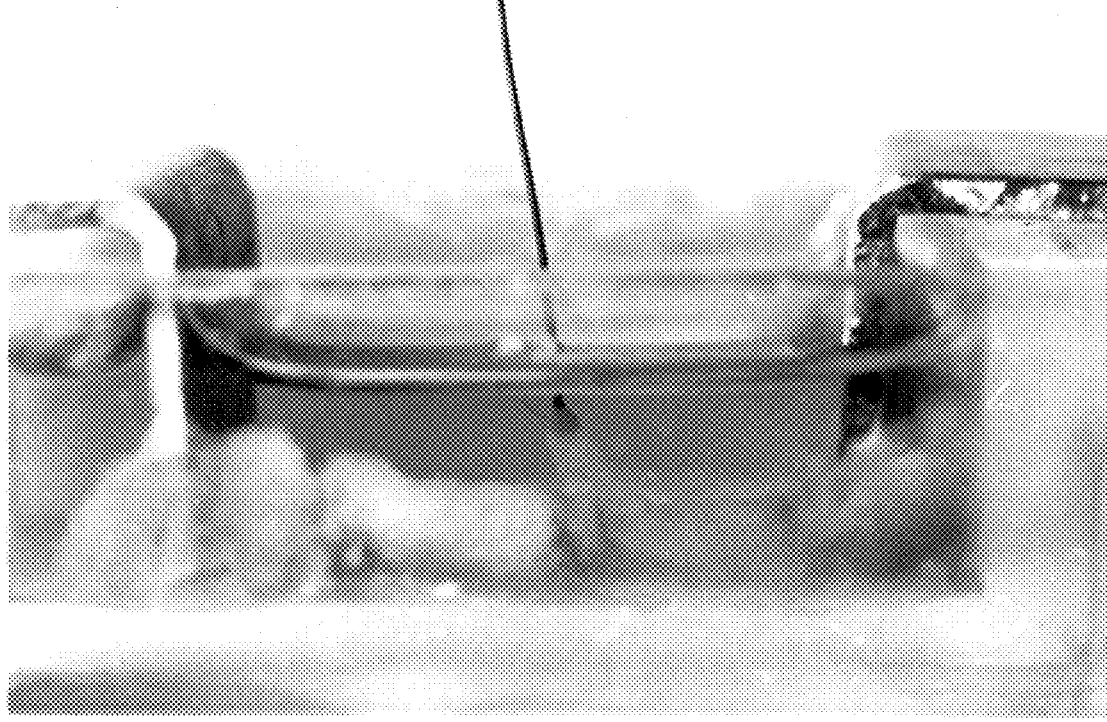
FIG. 8b is a photograph of a p(FA:SA) microsphere in the device of FIG. 1 being detached from porcine jejunum using the Cahn electrobalance.

Studies with microspheres containing barium sulfate demonstrated that some microspheres were retained in the gastrointestinal tract for as much as 28 hours. Using surface microscopy techniques, further analysis showed that the microspheres did tend to attach to the surface of the intestine. In a typical experiment, five rats were fed with polyanhydride microspheres made of poly[bis(p-carboxy phenoxy) propane-co-sebacic] (P[CPP-SA]) 20:80. The size of microspheres varied from 300 to 400 microns. 100 mg of spheres were suspended in 2 ml of distilled water and force-fed using a Gavage needle (gauge 16). Five hours after feeding, the rats were sacrificed by $CO_2$ asphyxiation and their intestines opened. Microspheres were found in the intestine, some sticking to the food, others adhering to the tissue. The areas with spheres adhering to the tissue were washed with saline. The tissue was fixed in neutral 10% formaldehyde solution for 24 hr. After fixation, the tissue was exposed to increasing concentrations of alcohol solutions, starting from 50:50% water and ethanol, and ending with 100% ethanol. At that stage, the tissue was dried using a $CO_2$ critical drying process. The dry samples were coated with gold-palladium and analyzed under a scanning electron microscope. A typical example of microspheres adhering to the intestine wall is shown in FIG. 8.

EXAMPLE 4

Preparation of Polyacrylamide Microspheres with High Bioadhesive Forces.

Preparation of Microspheres.

Polyacrylamide microspheres were produced by polymerizing an aqueous emulsion of acrylamide and bis methacrylamide in hexane. The following stock solutions were used:

1. 30% acrylamide (w/v), 10% bismethylacrylamide (w/v) in distilled water. The stock solution was treated with mixed bed ion-exchange resins to remove acrylic acid normally found in commercial preparations.

2. 1.2 M Tris pH 7.7.

3. 40% ammonium persulfate (w/v)

4. TEMED (N,N,N',N'-Tetramethylethylenediamine 2 ml of the acrylamide stock, 1 ml of Tris stock, 0.1 ml of ammonium persulfate and 2 ml of distilled water to make a final volume of 5.1 ml of 12% acrylamide/4% bis methylacrylamide solution. This working solution was extensively degassed under water vacuum to remove dissolved oxygen which might inhibit the polymerization reaction.

The acrylamide solution was added dropwise to 300 ml of n-hexane which was stirred at a rate of about 500 rpm with an overhead stirrer. Approximately 0.25 ml of SPAN 25 85 was added to the solution to prevent aggregation of the emulsion droplets. The stirring was generally maintained for 1–2 min until the emulsion reached the approximate desired size. To initiate polymerization, 1 ml of TEMED was added to the n-hexane phase and stirring was continued for 30 min. The beads were harvested and separated according to size by passing the solution through a series of graded sieves. Spheres having a diameter of between 300 and 800 $\mu M$ were selected for further studies.

EXAMPLE 5

Surface Activation of the Polyacrylamide Microspheres.

Polyacrylamide microspheres were treated with 1 liter carbonyldimiazole (CDI) to covalently attach cation agents such as polyethyleneimine or poly-1-lysine. Typically one half-batch of the polyacrylamide beads were incubated with 0.5 M sodium carbonate for 1 hr at 60° C. with shaking. The sodium carbonate solution was changed twice with fresh solution during the incubation. This procedure is thought to hydrolyze the beads and produce free carboxyl groups which might be available for CDI reaction.

Next the beads were solvent-exchanged with two changes of dry acetone and then incubated with 0.4% CDI (w/v) in acetone for 1 hr at 25° C. The incubation was repeated for an additional hour with fresh CDI solution. The beads were then washed twice with acetone to remove unbound CDI and then incubated with 10% polyethyleneimine (w/v), MW 1800) or else 1% poly-1-lysine in 0.2 M sodium borate buffer, pH 9.0 at 4° C. for 24 hrs. Alternatively, or in addition, one could add sialic acid to the polymer. The beads were washed twice with borate buffer and stored in 2 M ammonium chloride until needed. The ammonium chloride was used to inactivate "free" CDI binding sites. The beads were washed three times with 10 mM Tris, pH 7. immediately before use.

Microspheres can be tested by the "Sprinkle Test" as follows. Microspheres are sprinkled over excised intestinal tissue segments. These segments were then placed in a buffer solution and left to incubate at 4° C. on a slowly moving shaker for 30 minutes. The samples were then analyzed with a dissecting stereo microscope.

| POLYMER | COATING | CAHN FORCE |
|---|---|---|
| p(FA:SA) | well coated | approximately 26 mg |
| polyacrylamide | | approximately 10 mg |
| CDI/Polyacrylamide | blanket of $\mu$spheres | approximately 20 mg |
| p(CPP:SA) | scattered | approximately 8 mg |

EXAMPLE 6

Comparative In Vitro Test of Bead Attachment to Rat Intestine

Another way of comparing the relative bioadhesion capabilities of the microspheres was to incubate the different polymer particles with isolated rat intestine under physiological conditions. Typically, the jejunum from a newly sacrificed rat was removed, flushed with about 10 ml of Krebs Ringer saline, inverted on a stainless steel rod and divided into segments for testing. The segments were fashioned into empty sacs by attaching sutures to the cut ends.

This step prevented the binding of microspheres to the serosal surface of the gut. The intestinal sacs were then incubated with a known number of microspheres of defined size range for a period of 30 min at 4° C. at shaking rate of about 30 r.p.m. At the end of the test period, the number of bead that attached to the intestine were counted as well as the number of unattached microspheres. The results of a typical experiment are described below.

| Polymer | Attached | Unattached | Total |
| --- | --- | --- | --- |
| P(CPP:SA) | 24 | 261 | 285 |
| P(FA:SA) | 53 | 10 | 63 |
| Acrylamid | 113 | 220 | 330 |
| CDI-Acryl | 243 | 406 | 649 |

| Polymer | % Binding | Sac Length | Beads bound/cm sac |
| --- | --- | --- | --- |
| P(CPP:SA) | 8.4 | 3.0 cm | 8 |
| P(FA:SA) | 84.1 | 4.8 cm | 11 |
| Acrylamide | 33.9 | 2.8 cm | 40 |
| CDI-Acryl | 37.4 | 4.1 cm | 59 |

Modifications and variations of the method and bioadhesive microsphere compositions described herein will be obvious to those skilled in the art from the foregoing detailed description. Such modifications and variations are intended to come within the scope of the appended claims.

We claim:

1. A method for delivering a compound to a patient comprising administering to a mucosal membrane of a patient in need thereof an effective amount of a compound within a microparticle fabricated using a method yielding a morphology and particle diameter with a polymeric surface with an adhesive force of between 110 N/m$^2$ and 5000 N/M$^2$ as measured on living rat intestine, wherein the polymer is selected from the group consisting of synthetic polymers and hydrophilic proteins.

2. The method of claim 1 wherein the polymer is selected from the group of polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes, polyurethanes, polystyrene, polymers of acrylic and methacrylic esters, polylactides, poly(butyric acid), poly(valeric acid), poly(lactide-co-glycolide), polyanhydrides, polyorthoesters, poly(fumaric acid), poly(maleic acid), blends and copolymers of these polymers.

3. The method of claim 1 wherein the polymer is a synthetic polysaccharide.

4. The method of claim 1 wherein the polymer forms the microparticle.

5. The method of claim 1 wherein the polymer is coated onto the surface of a microparticle formed of a different material.

6. The method of claim 1 wherein the compound is selected from the group consisting of proteins, polysaccharides, inorganic compounds, and organic compounds.

7. The method of claim 6 wherein the compound is selected from the group consisting of hormones, enzymes, antigens, digestive aids, ulcer treatments, antihypertensives, enzyme inhibitors, antiparasitics, spermacides, antihemorrhoidal treatments, and radiopaque compounds.

8. The method of claim 1 wherein the microparticles are administered in combination with a pharmaceutical carrier.

9. The method of claim 1 wherein the microparticles are administered nasally.

10. The method of claim 1 wherein the microparticles are administered orally.

11. The method of claim 1 wherein the microparticles contain a compound detectable by imaging and are administered orally to a patient, wherein the gastrointestinal tract of the patient is imaged based on the location of the microspheres in the gastrointestinal tract.

* * * * *